United States Patent [19]

Coleman

[11] 4,156,787

[45] May 29, 1979

[54] ONE-STEP DEHYDROHALOGENATION-REARRANGEMENT-HYDROGENATION OF 1,1-BIS(4-HYDROXYARYL)-2-HALOETHANES

[75] Inventor: James P. Coleman, Maryland Heights, Mo.

[73] Assignee: Monsanto Company, St. Louis, Mo.

[21] Appl. No.: 846,754

[22] Filed: Oct. 31, 1977

[51] Int. Cl.$^2$ ............................................. C07C 39/16
[52] U.S. Cl. ................................... 568/729; 560/138
[58] Field of Search ........................ 568/729; 560/138

[56] References Cited

U.S. PATENT DOCUMENTS

| 3,444,245 | 5/1969 | Sieber | 260/613 A |
| 3,624,162 | 11/1971 | Sieber | 568/729 |
| 3,683,009 | 8/1972 | Middleton | 260/613 A |

OTHER PUBLICATIONS

Sieber, Ann. 730, 31–46 (1969).

*Primary Examiner*—Jane S. Myers
*Attorney, Agent, or Firm*—Wendell W. Brooks; Joseph D. Kennedy; James W. Williams, Jr.

[57] ABSTRACT

Dehydrohalogenation-rearrangement-hydrogenation of 1,1-bis(4-hydroxyaryl)-2-haloethanes in an aliphatic carboxylic acid solvent containing a carboxylic acid salt in the presence of gaseous hydrogen and a hydrogenation catalyst is effected in one step to yield 1,2-bis(4-hydroxyaryl)ethanes. The process is particularly directed to the production of 1,2-bis(4-hydroxyphenyl)ethane from 1,1-bis(4-hydroxyphenyl)-2-chloroethane.

16 Claims, No Drawings

ONE-STEP DEHYDROHALOGENATION-REARRANGEMENT-HYDROGENATION OF 1,1-BIS(4-HYDROXYARYL)-2-HALOETHANES

BACKGROUND OF THE INVENTION

This invention relates to the preparation of 1,2-bis(4-hydroxyaryl)ethanes. More specifically, it relates to a one-step dehydrohalogenation-rearrangement-hydrogenation of 1,1-bis(4-hydroxyaryl)-2-haloethanes under suitable conditions to yield the corresponding 1,2-bis(4-hydroxyaryl)ethanes, particularly 1,2-bis(4-hydroxyphenyl)ethane from 1,1-bis(4-hydroxyphenyl)-2-chloroethane.

The dehydrohalogenation-rearrangement of 1,1-bis(4-hydroxyaryl)-2-haloethanes to 4,4'-dihydroxystilbenes is known in the art. The reaction is effected under strongly basic and rather drastic conditions by heating the compound in a solution of potassium hydroxide or sodium hydroxide in methanol or ethanol at the boiling point of the solvent, followed by further heating of the dehydrohalogenated product in a high-boiling solvent selected from the group consisting of ethylene glycol, diethylene glycol monomethyl ether (methyl carbitol), and nitrobenzene to the boiling point of such solvent. The reaction may also be effected in one step by heating the 1,1-bis(4-hydroxyaryl)-2-haloethane directly in a solution of potassium hydroxide or sodium hydroxide in a high-boiling solvent selected from the above list. These processes of preparing 4,4'-dihydroxystilbenes are disclosed in Sieber, U.S. Pat. No. 3,624,162. However, it is apparent that if the corresponding saturated compounds, 1,2-bis(4-hydroxyaryl)ethanes, are desired, a separate hydrogenation step must be employed. The procedural requirements associated with the separate hydrogenation step-first, production and isolation of the 4,4'-dihydroxystilbene, and second, hydrogenation of the 4,4'-dihydroxystilbene—are very time consuming and inconvenient. Moreover, the procedure is not easily adapted to large technical scale operations.

The disadvantages encountered in the strongly basic, high-boiling solvent processes of the prior art are overcome by the discovery that the dehydrohalogenation-rearrangement-hydrogenation of 1,1-bis(4-hydroxyaryl)-2-haloethanes can be readily accomplished in a one-step process under suitable acidic reaction conditions to yield 1,2-bis(4-hydroxyaryl)ethanes.

SUMMARY OF THE INVENTION

According to the present invention, it has been discovered that 1,1-bis(4-hydroxyaryl)-2-haloethanes can undergo a one-step dehydrohalogenation-rearrangement-hydrogenation to yield the corresponding 1,2-bis(4-hydroxyaryl)ethanes. The process comprises contacting the 1,1-bis(4-hydroxyaryl)-2-haloethane in an aliphatic carboxylic acid solvent containing a carboxylic acid salt at dehydrohalogenation-rearrangement-hydrogenation conditions with gaseous hydrogen and a hydrogenation catalyst for a time sufficient to cause dehydrohalogenation-rearrangement-hydrogenation of the 1,1-bis(4-hydroxyaryl)-2-haloethane.

The 1,2-bis(4-hydroxyaryl)ethane products obtained in the present process can be recovered by any number of wellknown and conventional procedures as the free dihydroxy compounds or derivatives thereof, such as, for example, the corresponding diacyloxy compounds.

DETAILED DESCRIPTION OF THE INVENTION

Dehydrohalogenation-rearrangement-hydrogenation of 1,1-bis(4-hydroxyaryl)-2-haloethanes can be accomplished in one step under suitable acidic reaction conditions to yield 1,2-bis(4-hydroxyaryl)ethanes.

In accordance with the present process, the 1,1-bis(4-hydroxyaryl)-2-haloethane is contacted in an aliphatic carboxylic acid solvent containing carboxylic acid salt at dehydrohalogenation-rearrangement-hydrogenation conditions with gaseous hydrogen and a hydrogenation catalyst for a time sufficient to cause dehydrohalogenation-rearrangement-hydrogenation of the 1,1-bis(4-hydroxyaryl)-2-haloethane.

Suitable 1,1-bis(4-hydroxyaryl)-2-haloethanes which can be used to effect the one-step dehydrohalogenation-rearrangement-hydrogenation according to the present process are in general represented by the formula:

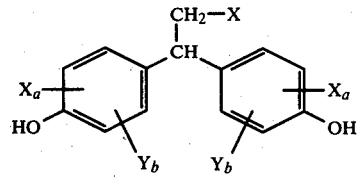

in which X independently represents a halogen selected from the group consisting of chlorine, bromine, and iodine; Y independently represents a non-interfering hydrocarbyl group, including, for example, lower alkyl of 1 to 6 carbon atoms and phenyl; and a and b each independently represent an integer from zero(0) to 4, inclusive, with the proviso that the sum of a and b, with respect to each aryl ring, does not exceed 4.

The term "non-interfering hydrocarbyl group" is employed herein to mean a hydrocarbon group which can be present in the 1,1-bis(4-hydroxyaryl)-2-haloethane without rendering the dehydrohalogenation-rearrangement-hydrogenation reaction substantially inoperative under process conditions. Such groups, as noted hereinabove, include alkyl of 1 to 6 carbon atoms and phenyl.

Of the halogens present in the 1,1-bis(4-hydroxyaryl)-2-haloethanes, chlorine is generally preferred in that the compounds, when employed as the organo-chlorides, as well as the chloride ion released during the course of the one-step dehydrohalogenation-rearrangement-hydrogenation exhibit less tendency to deactivate or poison the hydrogenation catalyst. This problem, however, is substantially reduced or even eliminated altogether when, as noted hereinbelow, palladium on charcoal is employed as the hydrogenation catalyst.

Representative of 1,1-bis(4-hydroxyaryl)-2-haloethanes suitable for use in the present process are 1,1-bis(4-hydroxyphenyl)-2-chloroethane, 1,1-bis(4-hydroxyphenyl)-2-bromoethane, 1,1-bis(4-hydroxyphenyl)-2-iodoethane, 1,1-bis(4-hydroxy-2-methylphenyl)-2-chloroethane, 1,1-bis(4-hydroxy-2-methylphenyl)-2-bromoethane, 1,1-bis(4-hydroxy-2-methylphenyl-2-iodoethane, 1,1-bis(4-hydroxy-3-methylphenyl)-2-chloroethane, 1,1-bis(4-hydroxy-3-methylphenyl)-2-bromoethane, 1,1-bis(4-hydroxy-3-methylphenyl)-2-iodoethane, 1,1-bis(2,3-dimethyl-4-hydroxyphenyl)-2-chloroethane, 1,1-bis(2,3-dimethyl-4-hydroxyphenyl)-2-bromoethane, 1,1-bis(2,3-dimethyl-4-hydroxyphenyl)-2-iodoethane, 1,1-bis(2,5-dimethyl-4-hydroxyphenyl)-2- chloroethane, 1,1-bis(2,5-dimethyl-4-hydroxyphenyl)-2-bromoethane, 1,1-bis(2,5-dimethyl-4-hydroxyphenyl)-2-iodoethane, 1,1-bis(2,6-dimethyl-4-hydroxyphenyl)-2-chloroethane, 1,1-bis(2,6-dimethyl-4-hydroxyphenyl)-2-bromoethane, 1,1-bis(2,6-dimethyl-4-hydroxyphenyl)-2-iodoethane, 1,1-bis(3,5-dimethyl-4-hydroxyphenyl)-2-chloroethane, 1,1-bis(3,5-dimethyl-4-hydroxyphenyl)-2-bromoethane, 1,1-bis(3,5-dimethyl-4-hydroxyphenyl)-2-iodoethane, 1,1-bis(3,6-dimethyl-4-hydroxyphenyl)-2-chloroethane, 1,1-bis(3,6-dimethyl-4-hydroxyphenyl)-2-bromoethane, 1,1-bis(3,6-dimethyl-4-hydroxyphenyl)-2-iodoethane, 1,1-bis(2,3-diethyl-4-hydroxyphenyl-2-chloroethane, 1,1-bis(2,3-diethyl-4-hydroxyphenyl)-2-bromoethane, 1,1-bis(2,3-diethyl-4-hydroxyphenyl)-2-iodoethane, 1,1-bis(2,5-diethyl-4-hydroxyphenyl)-2-chloroethane, 1,1-bis(2,5-diethyl-4-hydroxyphenyl)-2-bromoethane, 1,1-bis(2,5-diethyl-4-hydroxyphenyl)-2-iodoethane, 1,1-bis(2,6-diethyl-4-hydroxyphenyl)-2-chloroethane, 1,1-bis(2,6-diethyl-4-hydroxyphenyl)-2-bromoethane, 1,1-bis(2,6-diethyl-4-hydroxyphenyl)-2-iodoethane, 1,1-bis(3,5-diethyl-4-hydroxyphenyl)-2-chloroethane, 1,1-bis(3,5-diethyl-4-hydroxyphenyl)-2-bromoethane, 1,1-bis(3,5-diethyl-4-hydroxyphenyl)-2-iodoethane, 1,1-bis(3,6-diethyl-4-hydroxyphenyl)-2-chloroethane, 1,1-bis(3,6-diethyl-4-hydroxyphenyl)-2-bromoethane, 1,1-bis(3,6-diethyl-4-hydroxyphenyl)-2-iodoethane, 1,1-bis(3,5-di-t-butyl-4-hydroxyphenyl)-2-chloroethane, 1,1-bis(3,5-di-t-butyl-4-hydroxyphenyl-2-bromoethane, 1,1-bis(3,5-di-t-butyl-4-hydroxyphenyl)-2-iodoethane, 1,1-bis(4-hydroxy-2,3,5-trimethylphenyl)-2-chloroethane, 1,1-bis(4-hydroxy-2,3,5-trimethylphenyl)-2-bromoethane, 1,1-bis(4-hydroxy-2,3,5-trimethylphenyl)-2-iodoethane, 1,1-bis(4-hydroxy-2,3,6-trimethylphenyl)-2-chloroethane, 1,1-bis(4-hydroxy-2,3,6-trimethylphenyl)-2-bromoethane, 1,1-bis(4-hydroxy-2,3,6-trimethylphenyl)-2-iodoethane, 1,1-bis(2,3-dimethyl-4-ethyl-4-hydroxyphenyl)-2-chloroethane, 1,1-bis(2,3-dimethyl-5-ethyl-4-hydroxyphenyl)-2-bromoethane, 1,1-bis(2,3-dimethyl-5-ethyl-4-hydroxyphenyl)-2-iodoethane, 1,1-bis(2,5-dimethyl-3-ethyl-4-hydroxyphenyl)-2-chloroethane, 1,1-bis(2,5-dimethyl-3-ethyl-4-hydroxyphenyl)-2-bromoethane, 1,1-bis(2,5-dimethyl-3-ethyl-4-hydroxyphenyl)-2-iodoethane, 1,1-bis(2-chloro-4-hydroxyphenyl)-2-chloroethane, 1,1-bis(2-chloro-4-hydroxyphenyl)-2-bromoethane, 1,1-bis(2-chloro-4-hydroxyphenyl)-2-iodoethane, 1,1-bis(2-bromo-4-hydroxyphenyl)-2-chloroethane 1,1-bis(2-bromo-4-hydroxyphenyl)-2-bromoethane, 1,1-bis(2-bromo-4-hydroxyphenyl)-2-iodoethane, 1,1-bis(2-iodo-4-hydroxyphenyl)-2-chloroethane, 1,1-bis(2-iodo-4-hydroxyphenyl)-2-bromoethane, 1,1-bis(2-iodo-4-hydroxyphenyl)-2-iodoethane, 1,1-bis(4-hydroxy-2,3,5,6-tetramethylphenyl)-2-chloroethane, 1,1-bis(4-hydroxy-2,3,5,6-tetramethylphenyl)-2-bromoethane, 1,1-bis(4-hydroxy-2,3,5,6-tetramethylphenyl)-2-iodoethane, and the like.

Other compounds similarly oriented but having a different numbering designation because of rules of nomenclature are also suitable for use in the present process. Such compounds include those wherein the X substituent on each aryl ring represents a different halogen, and phenyl substituted compounds, for example, biphenyls. Illustrative examples include 1-(3-bromo-4-hydroxyphenyl)-1-(3-chloro-4-hydroxyphenyl)-2-chloroethane, 1-(3-bromo-4-hydroxyphenyl)-1-(3-chloro-4-hydroxyphenyl)-2-bromoethane, 1-(3-bromo-4-hydroxyphenyl)-1-(3-chloro-4-hydroxyphenyl)-2-iodoethane, 1,1-bis-[2,(5-hydroxybiphenyl)]-2-chloroethane [1,1-bis(4-hydroxy-2-phenylphenyl)-2-chloroethane], 1,1-bis[2-(5-hydroxybiphenyl)]-2-bromoethane [1,1-bis(4-hydroxy-2-phenylphenyl)-2-bromoethane], 1,1-bis[2-(5-hydroxybiphenyl)]-2-iodoethane [1,1-bis(4-hydroxy-2-phenylphenyl)-2-iodoethane], and the like.

Of the compounds suitable for use in the present process, the 1,1-bis(4-hydroxyphenyl)-2-haloethanes are of particular importance in that the product 1,2-bis(4-hydroxyphenyl)ethane (bisphenol E or simply BPE), is used as an intermediate in the preparation of polycarbonates, polyesters, and other synthetic materials. Of these, 1,1-bis(4-hydroxyphenyl)-2-chloroethane is especially important in that neither the compound itself, as an organo-chloride, nor the chloride ion released during the course of the one-step dehydrohalogenation-rearrangement-hydrogenation process exhibit any substantial tendency to deactivate or poison altogether the hydrogenation catalysts suitable for use in the present process.

As indicated hereinabove, the one-step dehydrohalogenation-rearrangement-halogenation of the present invention is carried out by contacting the 1,1-bis(4-hydroxyaryl)-2-haloethane in an aliphatic carboxylic acid solvent containing carboxylic acid salt at dehydrohalogenation-rearrangement-hydrogenation conditions with gaseous hydrogen and a hydrogenation catalyst for a time sufficient, in general between about 2 hours and about 5 hours for substantially complete reaction in batch operations, to yield the 1,2-bis(4-hydroxyphenyl)ethane product. It will, of course, be recognized that continuous operations are not so restricted in that unreacted starting material can be recycled for further reaction.

The reaction of the present invention can in general be illustrated:

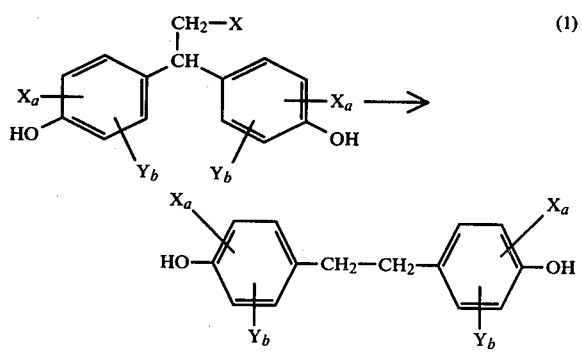

(1)

in which X and Y, and a and b are as defined hereinabove. Equation (2) illustrates a specific embodiment of the present invention, the one-step dehydrohalogenation-rearrangement-hydrogenation of 1,1-bis(4-hydroxyphenyl)-2-chloroethane to yield 1,2-bis(4-hydroxyphenyl)ethane, also known as bisphenol E or simply BPE.

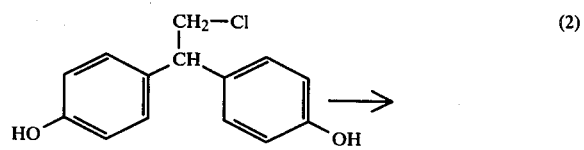

(2)

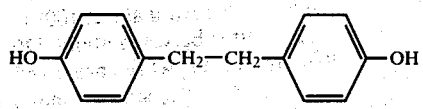

The aliphatic carboxylic acid solvents desirable for use in the present invention must be compatible with the present process. That is, the carboxylic acid solvent (a) should be inert under reaction conditions; (b) should dissolve the 1,1-bis(4-hydroxyaryl)-2-haloethane starting material; (c) should dissolve the carboxylic acid salt, all of which are preferred. Carboxylic acid solvents which satisfy these preferred requirements permit the one-step dehydrohalogenation-rearrangement-hydrogenation to proceed at a reasonable rate without complications and difficulties. In addition, the carboxylic acid solvent preferably should be substantially anhydrous. It will be noted, however, that small amounts of water within the range of about 10 percent or lower to about 15 percent cause no adverse effects upon the course and yield of the reaction, and solvents containing such amounts of water are suitable.

Exemplary of the aliphatic carboxylic acid solvents which meet the above requirements are the $C_2$ to $C_6$ aliphatic carboxylic acids. Of these, those preferred are the $C_2$ and $C_3$ carboxylic acids, with the $C_2$ carboxylic acid, acetic acid, being most preferred in that it is relatively inexpensive and readily available in substantially anhydrous form.

The aliphatic carboxylic acid solvent in which the 1,1-bis(4-hydroxyaryl)-2-haloethane is contacted must contain carboxylic acid salt. The salt preferably is soluble in the aliphatic carboxylic acid employed as solvent to form a homogeneous solution thereof. Exemplary of such salts are the alkali metal—lithium, sodium, potassium, rubidium, and cesium—carboxylic acid salts, the alkaline earth metal—magnesium, calcium, and barium—carboxylic acid salts, and quaternary ammonium—tetramethylammonium, tetraethylammonium, tetra-n-propylammonium, tetra-n-butylammonium, n-butyltri-n-propylammonium and the like—carboxylic acid salts. The alkaline earth metal salts and the quaternary ammonium salts, however, are generally more expensive and usually offer no particular advantage over the alkali metal carboxylic acid salts.

While any carboxylic acid salt can in general be employed so long as it is sufficiently soluble in the aliphatic carboxylic acid solvent and causes no adverse side reactions, it is preferred to employ the alkali metal salts of the $C_2$ to $C_6$ aliphatic carboxylic acids employed as solvents. And further, it is found in practice that the alkali metal carboxylic acid salt corresponding to the aliphatic carboxylic acid employed as solvent is most preferred. Thus, since acetic acid is the most preferred aliphatic carboxylic acid solvent, the alkali metal acetates, particularly sodium acetate, are the most preferred salts.

It will be apparent to those skilled in the art that the pre-formed carboxylic acid salt can be employed. However, when the carboxylic acid salt is that which corresponds to the aliphatic carboxylic acid solvent being employed, it can either be charged directly—that is, as the pre-formed salt—to the carboxylic acid solvent, or alternatively, it can be formed in situ by charging an anhydrous hydroxide ion-containing compound. The cation of such compounds should preferably be an alkali metal ion, an alkaline earth metal ion, or a quaternary ammonium ion. Thus the carboxylic acid salt can be formed in situ by charging an alkali metal, such as, for example, lithium hydroxide, sodium hydroxide, potassium hydroxide, rubidium hydroxide, and cesium hydroxide, an alkaline earth metal hydroxide, such as, for example, magnesium hydroxide, calcium hydroxide, and barium hydroxide, or a quaternary ammonium hydroxide, such as, for example, tetraethylammonium hydroxide, tetra-n-propylammonium hydroxide, tetra-n-butylammonium hydroxide, in appropriate amounts to the aliphatic carboxylic acid solvent. For example, when glacial acetic acid is the aliphatic carboxylic acid solvent, the charging of sodium hydroxide thereto produces sodium acetate in situ in an amount equivalent to the amount of added sodium hydroxide.

Of the hydroxide ion-containing compounds suitable for use in the present process, the alkali metal hydroxides are preferred. Of these, sodium hydroxide is most preferred in that the resulting sodium salt is in general highly soluble in the corresponding aliphatic carboxylic acid. Moreover, sodium hydroxide is relatively inexpensive and readily available.

The hydrogenation catalyst can be any of a number of well known catalysts. However, such catalysts must be compatible with the one-step process of the present invention. That is, the hydrogenation catalyst must cause little, if any, adverse effect upon either the course of the desired reaction or the yield of the 1,2-bis(4-hydroxyaryl)ethane product.

The most common hydrogenation catalysts are the noble or platinum metals—platinum, palladium, rhodium, and ruthenium. Copper chromium oxide (copper chromite) and nickel are also used, although they generally cannot be used with strongly acidic solvents because they tend to dissolve. Similarly, catalysts that are otherwise deactivated under acidic reaction conditions cannot be used with acidic solvents.

Hydrogenations over platinum frequently employ finely divided metallic platinum obtained by the hydrogenation of a platinum compound such as platinum oxide ($PtO_2$) in the hydrogenation apparatus, whereas palladium, rhodium, ruthenium catalysts are usually deposits of the metal on the surface of an inert support such as carbon (charcoal), barium sulfate, calcium carbonate, or strontium carbonate. Catalysts formed by depositing platinum on an inert support are also used. It will be recognized by those skilled in the art, however, that the activity of a catalyst on an inert support is normally diminished as the support is changed from charcoal to barium sulfate to calcium or strontium carbonate. It will be further recognized that catalysts that are supported on metal carbonates cannot be employed in acidic solvents such as the aliphatic carboxylic acid solvents employed in the present invention.

Thus, among the noble metal catalysts suitable for use in the present process, palladium on charcoal, palladium on barium sulfate, palladium black, platinum oxide (Adam's catalyst), platinum black, platinum on charcoal, rhodium on charcoal, and the like are advantageously employed. Some of the least active Raney nickel catalysts, for example, W2 Raney nickel, may be similarly advantageous.

Of these hydrogenation catalysts, palladium catalysts are preferred in that, outside of some occasional catalyst deactivations, they are noted for their general resistance to catalyst poisons. Of these, palladium on charcoal is most preferred in that it is both highly active as well as selective. Moreoever, it is readily available commercially and/or easily prepared via known procedures.

For a general discussion of hydrogenation catalysts and their applications see Augustine, *Catalytic Hydrogenation*, Marcel Dekker, New York, 1965, and references cited therein. See also House, *Modern Synthetic Reactions*, 2nd ed., W. A. Benjamin, Menlo Park, CA, 1972, Chapter 1, pp. 1–44, and references cited therein.

The concentration of the 1,1-bis(4-hydroxyaryl)-2-haloethane employed in the process of the present invention is not extremely critical, although it will be noted that extremely high concentrations tend to cause a decrease in the yield of the desired 1,2-bis(4-hydroxyaryl)ethane products. In general, however, all that is necessary is that sufficient amounts be present in solution to permit the one-step dehydrohalogenation-rearrangement-hydrogenation thereof to proceed at a reasonable rate. Thus, although concentrations as low as 0.01 percent by weight, or even lower, in the aliphatic carboxylic acid solvent can be employed, for reasons of efficiency and economy, it is preferred to employ concentrations of from about 5 percent to about 20 percent by weight, or on a molar basis, from about 0.2 molar to about 0.8 molar, or even higher, of the 1,1-bis(4-hydroxyaryl)-2-haloethane.

The concentration of the carboxylic acid salt is determined in the first instance by the corresponding concentration of the 1,1-bis(4-hydroxyaryl)-2-haloethane employed. That is, for complete stoichiometric reaction, the concentration of the carboxylic acid salt is preferably present at least in the same gram-equivalent weight quantity (with respect to the aliphatic carboxylic acid anion) as the 1,1-bis(4-hydroxyaryl)-2-haloethane. Thus the gram-equivalent weight ratio of carboxylic acid salt to the 1,1-bis(4-hydroxyaryl)-2-haloethane is preferably at least 1:1. A slight excess, however, on the order of about 10 percent, may be beneficial. On the other hand, a less than 1:1 gram-equivalent weight ratio may cause unwanted side reactions to occur, and thereby reduce both the yield and purity of the desired 1,2-bis(4-hydroxyaryl)ethane product.

The quantity or amount of hydrogenation catalyst employed is not narrowly critical. The amount of catalyst used in the present process—as is usually the case for hydrogenation reactions in general—is between about 5 percent and about 10 percent of the weight of the 1,1-bis(4-hydroxyaryl)-2-haloethane starting material or substrate. It will be noted, however, that large-scale reactions in general require less and small scale reactions usually require more than this amount.

It will be apparent to those skilled in the art that the hydrogenation catalyst to 1,1-bis(4-hydroxyaryl)-2-haloethane weight ratio influences the rate of the reaction, with an increase in the amount of catalyst in general causing an increase in the reaction rate. The increase in rate, however, is much more pronounced when more catalyst is added to a reaction with a low hydrogenation catalyst to 1,1-bis(4-hydroxyaryl)-2-haloethane weight ratio than when it is added to one with a high ratio.

The dehydrohalogenation-rearrangement-hydrogenation conditions utilized in the present process can vary within fairly wide limits. It will be recognized, however, that the present process is temperature dependent in the sense that the reaction proceeds at an increased rate at higher temperatures. Excessively high temperatures are to be avoided in that the selectivity of the desired 1,2-bis(4-hydroxyaryl)ethane product may be adversely affected. Suitable temperatures will in general range from about 100° C. to about 250° C., with temperatures between about 120° C. and about 255° C. being preferred. At the preferred temperatures the reaction proceeds in a smooth manner and at a reasonable rate to yield the 1,2-bis(4-hydroxyaryl)ethane product.

The total initial pressure within the reaction vessel or autoclave for the gaseous hydrogen will generally range between about 10 pounds per square inch gauge (hereinafter, psig) and about 1000 psig. The upper limit, however, is not critical; it is imposed more for practical reasons than for reasons to avoid any adverse effect upon the yield and selectivity of the desired product. The preferred initial pressure, however, is between about 200 psig and about 500 psig.

The time required for the desired one-step dehydrohalogenation-rearrangement-hydrogenation to occur is not critical. Generally, a reaction time between about 2 hours and about 5 hours is required for complete reaction for batch operations, with about 3 hours usually being sufficient. It will, of course, be recognized, however, that the actual reaction time required will vary with the 1,1-bis(4-hydroxyaryl)-2-haloethane starting material and its concentration, the amount of hydrogenation catalyst employed, temperature, pressure, the mode of operation, and the like employed.

The present process is suited to either batch or continuous operations. Continuous operations can involve recirculation of the aliphatic carboxylic acid solvent along with any remaining carboxylic acid salt and unreacted 1,1-bis(4-hydroxyaryl)-2-haloethane starting material following isolation of the 1,2-bis(4-hydroxyaryl)ethane product. Additional 1,1-bis(4-hydroxyaryl)-2-haloethane starting material as well as carboxylic acid salt, hydrogenation catalyst, and gaseous hydrogen can then be charged to the reaction vessel to continue the process in a subsequent reaction.

The 1,2-bis(4-hydroxyaryl)ethane products obtained in the present process can be readily recovered by any number of well known and conventional procedures. It will be understood, however, that the isolation procedures employed in the procedural examples and discussed hereinbelow are primarily for illustrative purposes. Other procedures can be employed, and may be preferred, for commercial use.

Upon completion of the reaction, the product solution is cooled, usually to about 60° C., and filtered to remove the hydrogenation catalyst and any other insoluble solid material. The major portion of the aliphatic carboxylic acid solvent is thereafter evaporated to leave a residue comprising the unreacted phenol (if crude 1,1-bis(4-hydroxyaryl)-2-haloethane, prepared from an appropriate phenol and a monohaloacetaldehyde, is employed) and product. Distillation at reduced pressure at an appropriate temperature removes the remaining aliphatic carboxylic acid solvent and unreacted phenol. If desired, recrystallization of the crude residue may be effected from a suitable solvent such as ethanol, acetone, and the like to yield the pure 1,2-bis(4-hydroxyaryl)ethane.

Instead of being isolated as the free 1,2-bis(4-hydroxyaryl)ethane, the product is alternatively isolated as the corresponding diacyloxy compound. The crude product is treated with an appropriate acylating agent, for example, acetic anhydride (or a mixture of acetic anhydride and glacial acetic acid) and the like, and heated at an appropriate temperature for a time sufficient to smoothly convert the free 1,2-bis(4-hydroxyaryl)ethane to the corresponding 1,2-(4-acyloxyaryl)ethane. The crystalline solid which results upon cooling the reaction solution is collected, usually be suction filtration. Concentration of the filtrate produces additional 1,2-bis(4-acyloxyaryl)ethane which is similarly isolated. Recrystallization, if desired, can be effected from a suitable solvent such as an appropriate solution of acetic acid and acetic anhydride, ethanol, acetone, and the like to yield the pure product.

It will be noted that since the diacyloxy derivatives are esters, the free 1,2-bis(4-hydroxyaryl)ethane can, if desired, be readily recovered therefrom by standard and conventional procedures.

Thus the present invention provides a convenient one-step route from 1,1-bis(4-hydroxyaryl)-2-haloethanes (which can be prepared from appropriate phenols and monohaloacetaldehydes, including the acetals thereof, according to the examples set forth hereinbelow or according to procedures described in the prior art, for example, Seiber, U.S. Pat. No. 3,624,162) to 1,2-bis(4-hydroxyaryl)ethanes.

The following examples illustrate the present invention and the manner by which it can be practiced.

EXAMPLE 1

Procedure A

To a 1-liter jacketed resin kettle equipped with a mechanical stirrer, gas dispersion tube and thermometer, and cooled to −5° C. with circulated glycol-water thermostated cooling liquid, was charged 500 grams (5.8 moles) of vinyl acetate (inhibited with 300 parts per million diphenylamine) and 5.0 grams (0.039 mole) of N,N-dimethylcyclohexylamine. Chlorine gas (453.0 grams, 6.4 moles; calculated 412.0 grams, 5.8 moles) was bubbled into the stirred solution from a preweighed lecture bottle over a 4.25-hour period at a rate to maintain the reaction mixture's temperature at about 15° C. (approximately 500 milliliters per minute flow rate). A precipitate initially formed in the reaction mixture but dissolved after about 1 hour. After the 4.25-hour period, the vinyl acetate was completely consumed, as determined via nuclear magnetic resonance spectroscopy.

Nuclear magnetic resonance spectroscopic analysis of the product mixture showed the presence of 1,2-dichloroethyl acetate, chloroacetaldehyde, acetyl chloride, and unidentified derivatives of chloroacetaldehyde.

The crude 1,2-dichloroethyl acetate thus obtained was transferred to a 5-liter flask equipped with a mechanical stirrer and thermometer, and cooled in an ice bath. Absolute ethanol (1605.0 grams, 34.9 moles) was added to the stirred, cooled mixture over a 1-hour period at a rate sufficient to keep the temperature below 25° C. The first 30 percent of the addition was slow as the reaction is initially exothermic; the remaining 70 percent was added more quickly. The solution was allowed to stand, with stirring, at ambient temperatures overnight (about 16 hours), and thereafter heated under reflux for 1.5 hours. The reaction mixture was cooled to ambient temperatures and 300.0 grams (3.0 moles) of anhydrous calcium carbonate was added slowly (effervescence). Upon completion of the addition, the mixture was stirred for an additional 0.5 hour and concentrated on a rotary evaporator at approximately 60° C. using water-pump vacuum to collect 1576 grams of distillate. Ice water was added to the residue which separated into two layers with some undissolved solid (calcium carbonate). The solid was filtered out and the upper organic layer separated and dried over 3A molecular sieves to give 551.0 grams of crude chloroacetal. An additional 201.0 grams of chloroacetal was obtained by distillation of the distillate from above at atmospheric pressure through a 6-inch Vigreux column until the distillate temperature reached 150° C. to remove the low-boiling fraction and leave the product residue. The combined chloroacetal fractions (752.0 grams, 85 percent crude yield) were analyzed by gas chromatography and shown to be 90 percent pure chloroacetal, with the impurities comprising ethanol, ethyl acetate, and dichloroacetal.

Procedure B

The procedure described in Procedure A above was repeated with the exception that N,N-dimethylcyclohexylamine was excluded. The total yield of crude chloroacetal (90 percent pure) was 805.0 grams, 91 percent.

EXAMPLE 2

Dowex 50W-X8(H+), 100–200 mesh ion exchange resin (2,268.0 grams, 5.0 pounds; 50 percent water) was dried in a vacuum oven at 80° C. and placed in a 12-liter flask equipped with a mechanical stirrer, thermometer, and dropping funnel, and cooled with tap water in a cooling bath. Anhydrous phenol (2,724.0 grams, 29.0 moles; 6.0 pounds) and 3.0 liters of glacial acetic acid were added to the resin and stirring commenced. To the stirred mixture, initially at 26° C., was added 733.0 grams (4.8 moles or 4.3 moles based on 90 percent purity) of crude chloroacetal from EXAMPLE 1 above over a 10-minute period. Samples were removed periodically and analyzed by high pressure liquid chromatography (HPLC) to determine the ratio of condensation product to residual phenol. These ratios and reaction temperatures were as follows:

| Time (Minutes) | Temperature (° C.) | HO–C$_6$H$_4$–CH(CH$_2$Cl)–C$_6$H$_4$–OH / OH-C$_6$H$_5$ |
|---|---|---|
| 0 | 26 | 0.28 |
| 30 | 34 | 0.41 |
| 120 | 30 | 0.36 |
| 190 | 27 | 0.36 |
| 240 | 26 | 0.55 |
| 300 | 26 | 0.45 |
| 360 | 26 | 0.51 |
| 420 | 26 | 0.49 |

At the end of the reaction period (420 minutes, 7.0 hours), the reaction solution containing 1,1-bis(4-hydroxyphenyl)-2-chloroethane was removed from the resin through a sintered glass filter stick. The resin was washed with 3.0 liters of glacial acetic acid to remove any occluded material and filtered. The acetic acid wash and the reaction solution were separately allowed to stand overnight (approximately 16 hours).

The acetic acid wash solution was treated with 210.0 grams/5.25 moles) of solid sodium hydroxide and combined with the reaction solution containing the 1,1-bis(4-hydroxyphenyl)-2-chloroethane. The combined solutions were placed in a 5-gallon (18.9 liter) autoclave, and a slurry of 45.0 grams of 5 percent palladium on charcoal in 100 milliliters of glacial acetic acid (prepared under nitrogen) was added thereto. The autoclave was flushed with hydrogen three times, sealed, pressurized to 300 psig with hydrogen and heated to 140° C. for 3 hours. Hydrogen uptake began at about 110° C. and continued at a fairly rapid rate for about 0.5 hour, followed by a slow pressure drop, possibly due to a leak, during the remaining reaction time. The autoclave was cooled to about 60° C. and depressurized. The solution was removed, filtered while warm, and allowed to stand overnight (approximately 16 hours). The solvent was removed on a rotary evaporator at water-pump pressure to leave a semi-solid mixture of phenol plus products which was allowed to stand two days. The mixture was distilled at 15 milliliters of mercury pressure from a 5-liter flask heated with an electric heating mantle. After 1198.0 grams of distillate (phenol and acetic acid) had been collected, the distillation became very erratic because of poor stirring and was discontinued even though some phenol remained. The mixture was cooled and 473 milliliters (1 pint) of glacial acetic acid and 1893 milliliters of acetic anhydride added. The resulting mixture was heated, with stirring, to 120° C. over a 45-minute period, after which time all the solid material had dissolved, and cooled, with stirring, overnight. The solid material which crystallized was collected by suction filtration, washed with 250 milliliters of acetic acid and 500 milliliters of water, and dried in a vacuum oven to yield 208.0 grams of 1,2-bis(4-acetoxyphenyl)ethane of 95 percent purity as determined by gas chromatography. Recrystallization from 300 milliliters of a 4:1 mixture of acetic acid and acetic anhydride yielded 171.3 grams of pure 1,2-bis(4-acetoxyphenyl)ethane, melting point 115°–116° C.

The isolation filtrate was evaporated to about 1500 milliliters and cooled to induce crystallization. The resultant crystalline material was collected by suction filtration, washed successively with 250 milliliters of acetic acid and 500 milliliters of water, and dried in a vacuum oven to give 272.0 grams of 90 percent pure 1,2-bis(4-acetoxyphenyl)ethane. The crystals were recrystallized from 375 milliliters of 4:1 mixture of acetic acid and acetic anhydride to give 142.0 grams of 99 percent pure 1,2-bis(4-acetoxyphenyl)ethane, melting point 112°–115° C.

The crystallization liquors were combined, evaporated to about 100 milliliters, cooled, and filtered to yield an additional 47.0 grams of 1,2-bis(4-acetoxyphenyl)ethane.

The total yield of pure collected 1,2-bis(4-acetoxyphenyl)ethane was 360.3 grams (28.1 percent based on 4.3 actual moles of chloroacetal).

The reduced yield was due in part to a portion of the 1,2-bis(4-acetoxyphenyl)ethane product remaining in the residual isolation filtrate, which was shown by gas chromatographic analysis to contain greater than 30 percent of the product actually produced.

EXAMPLE 3

The procedure from EXAMPLE 2 above was repeated using the same resin (untreated since EXAMPLE 2) and 775.0 (5.08 moles or 4.6 moles based on 90 percent purity) of crude chloroacetal from EXAMPLE 1 above.

| TIME (Minutes) | Temperature (°C.) | HO–C$_6$H$_4$–CH(CH$_2$Cl)–C$_6$H$_4$–OH / phenol |
|---|---|---|
| 30 | 24 | 0.09 |
| 60 | 25 | 0.16 |
| 120 | 27 | 0.29 |
| 180 | 27 | 0.38 |
| 240 | 27 | 0.40 |
| 300 | 27 | 0.49 |
| 360 | 26 | 0.49 |
| 420 | 25 | 0.51 |

The one-step dehydrohalogenation-rearrangement-hydrogenation was repeated as described in EXAMPLE 2 with the exception that only 35.0 grams of 5 percent palladium on charcoal was employed. The catalyst was removed from the reaction mixture by filtration and the solution allowed to stand overnight (approximately 16 hours), during which time 1,2-bis(4-hydroxyphenyl)ethane crystallized. The crystalline solid was collected by suction filtration, washed successively with 250 milliliters of acetic acid and 2 liters of water, and dried in a vacuum oven to yield 260.0 grams of 1,2-bis(4-hydroxyphenyl)ethane. This material was acetylated by heating in a solution of 300 milliliters acetic acid and 350 milliliters of acetic anhydride. The solution was cooled and the resultant crystalline material collected by suction filtration to yield 234.5 grams of 1,2-bis(4-acetoxyphenyl)ethane.

The 1,2-bis(4-hydroxyphenyl)ethane isolation filtrate was distilled at atmospheric pressure to give 7.5 liters of distillate, boiling point up to 135° C., which comprised 80 percent acetic acid, 17 percent ethyl acetate, 3 percent water, all by weight, and trace amounts of phenol as determined by nuclear magnetic resonance spectroscopic analysis. The residue was further concentrated on a rotary evaporator at oil pump pressure (10 millimeters of mercury) to give an additional 2037.0 grams of distillate which comprised 68 percent phenol and 32 percent acetic acid, both by weight. The remaining residue (921.0 grams) was treated with 1200 milliliters of acetic anhydride, heated to reflux, and cooled, with stirring, overnight. The precipitated solid material was filtered off, washed successively with 200 milliliters of acetic acid and 1 liter of water, and dried in a vacuum oven to yield 150.0 grams of 1,2-bis(4-acetoxyphenyl)ethane. Additional product was isolated as described in EXAMPLE 2 above to give a total isolated yield of 525.1 grams (38.3 percent based on 4.6 actual moles of chloroacetal) of 1,2-bis(4-acetoxyphenyl)ethane of greater than 95 percent purity.

The 1,2-bis(4-hydroxyaryl)ethane products produced in the present process have many and varied utilities. For example, they are useful as bactericides, chemical intermediates, monomer units for copolymers, and antioxidants. They are used to stabilize such materials as animal and vegetable fats or oils, gasoline, lubricants, polyalkenes such as polyethylene and polypropylene, and both natural and synthetic rubber. They are also used in the preparation of resins, for example, polyesters, polycarbonates, and the like resins, wherein they are used as the dihydroxy compound which is reacted with phosgene, dibasic acids, dibasic acid halides, and the like.

While the invention has been described with respect to various specific examples and embodiments thereof, it will be understood that the invention is not limited thereto and that many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A process for the one-step dehydrohalogenation-rearrangement-hydrogenation of 1,1-bis(4-hydroxyaryl)-2-haloethanes, which process comprises contacting the 1,1-bis(4-hydroxyaryl)-2-haloethane in an aliphatic carboxylic acid solvent containing a soluble carboxylic acid salt at dehydrohalogenation-rearrangement-hydrogenation conditions including temperatures between about 100° C. and about 250° C. with gaseous hydrogen and a hydrogenation catalyst for a time sufficient to cause dehydrohalogenation-rearrangement-hydrogenation of the 1,1-bis(4-hydroxyaryl)-2-haloethane to yield the corresponding 1,2-bis(4-hydroxyaryl)ethane, with the aforesaid 1,1-bis(4-hydroxyaryl)-2-haloethanes being represented by the formula:

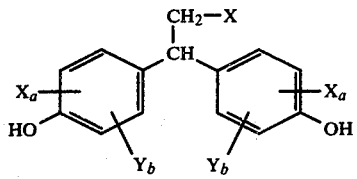

in which X independently represents a halogen selected from the group consisting of chlorine, bromine, and iodine; Y independently represents a non-interfering hydrocarbyl group; and a and b each independently represent an integer from zero (0) to 4, inclusive, with the proviso that the sum of a and b, with respect to each aryl ring, does not exceed 4.

2. The process of claim 1 wherein the 1,1-bis(4-hydroxyaryl)-2-haloethane is 1,1-bis(4-hydroxyphenyl)-2-chloroethane and the 1,2-bis(4-hydroxyaryl)ethane is 1,2-bis(4-hydroxyphenyl)ethane.

3. The process of claim 1 wherein the aliphatic carboxylic acid solvent is substantially anhydrous.

4. The process of claim 3 wherein the aliphatic carboxylic acid solvent comprises $C_2$ to $C_6$ aliphatic carboxylic acids.

5. The process of claim 4 wherein the $C_2$ to $C_6$ aliphatic carboxylic acid is acetic acid.

6. The process of claim 1 wherein the carboxylic acid salt is dissolved in the aliphatic carboxylic acid solvent to form a homogeneous solution thereof.

7. The process of claim 1 wherein the carboxylic acid salt is pre-formed.

8. The process of claim 7 wherein the pre-formed carboxylic acid salt is an alkali metal carboxylic acid salt.

9. The process of claim 8 wherein the pre-formed alkali metal carboxylic acid salt is sodium acetate.

10. The process of claim 1 wherein the carboxylic acid salt is formed in situ from the aliphatic carboxylic acid and added hydroxide ion-containing compound.

11. The process of claim 10 wherein the added hydroxide ion-containing compound is an alkali metal hydroxide and the carboxylic acid salt is an alkali metal carboxylic acid salt.

12. The process of claim 11 wherein the alkali metal hydroxide is sodium hydroxide, the aliphatic carboxylic acid is acetic acid, and the alkali metal carboxylic acid salt is sodium acetate.

13. The process of claim 1 wherein the hydrogenation catalyst is palladium on charcoal.

14. The process of claim 1 wherein the dehydrohalogenation-rearrangement-hydrogenation conditions comprise a total initial hydrogen pressure between about 10 psig and about 1000 psig.

15. The process of claim 1 wherein the time sufficient to cause dehydrohalogenation-rearrangement-hydrogenation is between about 2 hours and about 5 hours.

16. The process of claim 1 wherein the concentration of the 1,1-bis(4-hydroxyaryl)-2-haloethane in the aliphatic carboxylic acid solvent is between about 0.2 molar and about 0.8 molar; the gram-equivalent weight ratio of the carboxylic acid salt to the 1,1-bis(4-hydroxyaryl)-2-haloethane is at least 1:1; and the amount of hydrogenation catalyst employed is between about 5 percent and about 10 percent of the weight of the 1,1-bis(4-hydroxyaryl)-1,1-bis(4-hydroxyaryl)-2-haloethane employed.

* * * * *